(12) United States Patent
Masui et al.

(10) Patent No.: US 11,740,179 B2
(45) Date of Patent: Aug. 29, 2023

(54) GAS SENSING SYSTEM HAVING QUADRIC REFLECTIVE SURFACE

(71) Applicant: Lumileds LLC, San Jose, CA (US)

(72) Inventors: Hisashi Masui, Newark, CA (US); Oleg Borisovich Shchekin, San Francisco, CA (US); Franklin Chiang, Campbell, CA (US)

(73) Assignee: Lumileds LLC, San Jose, CA (US)

( * ) Notice: Subject to any disclaimer, the term of this patent is extended or adjusted under 35 U.S.C. 154(b) by 120 days.

(21) Appl. No.: 17/090,118

(22) Filed: Nov. 5, 2020

(65) Prior Publication Data

US 2021/0247312 A1 Aug. 12, 2021

Related U.S. Application Data

(60) Provisional application No. 63/093,978, filed on Oct. 20, 2020, provisional application No. 62/971,756, filed on Feb. 7, 2020.

(51) Int. Cl.
*G01N 21/15* (2006.01)
*G01N 21/61* (2006.01)
(Continued)

(52) U.S. Cl.
CPC ............. *G01N 21/61* (2013.01); *G01N 21/47* (2013.01); *G01N 33/0004* (2013.01);
(Continued)

(58) Field of Classification Search
CPC ........ G01N 21/61; G01N 21/47; G01N 21/49; G01N 21/3504; G01N 33/0004; G01N 33/004; G01N 33/0047
See application file for complete search history.

(56) References Cited

U.S. PATENT DOCUMENTS 5,471,299 A * 11/1995 Kaye .................. G01N 15/1436
356/336
7,635,845 B2 * 12/2009 Jensen ............... G01N 21/3518
250/338.5
(Continued)

FOREIGN PATENT DOCUMENTS

CN 106841038 A 6/2017
CN 109870414 6/2019
(Continued)

OTHER PUBLICATIONS

"International Application Serial No. PCT US2021 016921, International Search Report dated Jun. 1, 2021", 4 pgs.
(Continued)

*Primary Examiner* — Rebecca C Bryant
(74) *Attorney, Agent, or Firm* — Schwegman, Lundberg & Woessner, P.A.

(57) ABSTRACT

In a gas sensing system, a light emitter can emit light through a gas sample toward a concave reflective surface. The reflective surface can redirect the emitted light to propagate through the gas sample toward a light sensor. Using, optionally, the Beer-Lambert Law, the system can determine a concentration of the gas material in the gas sample. By selecting a specified shape for the reflective surface, such as a complete or partial ellipsoid, and locating the light emitter and the light sensor in specified locations, such as at one or both foci of the ellipsoid, the gas sensing system can reduce variation in optical path length, from optical path to optical path, in the light that propagates from the light emitter, to the reflective surface, and to the light sensor. Reducing the variation in optical path length can improve an accuracy in determining the concentration of the gas material.

16 Claims, 9 Drawing Sheets

(51) Int. Cl.
*G01N 33/00* (2006.01)
*G01N 21/47* (2006.01)

(52) U.S. Cl.
CPC ....... *G01N 33/004* (2013.01); *G01N 33/0047* (2013.01); *G01N 2201/0631* (2013.01); *G01N 2201/0636* (2013.01)

(56) References Cited

U.S. PATENT DOCUMENTS

| | | | |
|---|---|---|---|
| 8,193,502 B2* | 6/2012 | Hodgkinson | G01N 21/3504 250/343 |
| 10,254,161 B2* | 4/2019 | Lee | G01N 21/031 |
| 10,613,028 B2 | 4/2020 | Lee et al. | |
| 2006/0226367 A1* | 10/2006 | Hopkins | G01N 21/031 250/343 |
| 2007/0085023 A1* | 4/2007 | Debroche | G01N 21/0303 356/440 |
| 2007/0114421 A1 | 5/2007 | Maehlich et al. | |
| 2016/0231244 A1 | 8/2016 | Camargo et al. | |
| 2018/0259452 A1 | 9/2018 | Li et al. | |
| 2019/0165778 A1* | 5/2019 | Kuring | G05F 3/245 |
| 2022/0211890 A1* | 7/2022 | Duck | C02F 1/325 |

FOREIGN PATENT DOCUMENTS

| | | | | |
|---|---|---|---|---|
| CN | 209979482 U | * | 1/2020 | |
| GB | 2537994 | * | 11/2016 | ............... A61B 3/12 |
| KR | 100494103 B1 | | 6/2005 | |
| KR | 100732709 B1 | | 6/2007 | |
| KR | 20100115098 | | 10/2010 | |
| KR | 101895236 B1 | | 9/2018 | |
| WO | 2018210583 | | 11/2018 | |

OTHER PUBLICATIONS

"International Application Serial No. PCT US2021 016921, Written Opinion dated Jun. 1, 2021", 5 pgs.

"International Application Serial No. PCT/US2021/016933, International Search Report dated Jun. 1, 2021", 3 pgs.

"International Application Serial No. PCT/US2021/016933, Written Opinion dated Jun. 1, 2021", 5 pgs.

"International Application Serial No. PCT/US2021/016921, International Preliminary Report on Patentability dated Aug. 18, 2022", 7 pgs.

"International Application Serial No. PCT/US2021/016933, International Preliminary Report on Patentability dated Aug. 18, 2022", 7 pgs.

\* cited by examiner

GAS SENSING SYSTEM HAVING QUADRIC REFLECTIVE SURFACE

CROSS-REFERENCE TO RELATED APPLICATIONS

This application claims the benefit of U.S. Provisional Application No. 62/971,756, filed Feb. 7, 2020 and entitled, "GAS SENSOR PACKAGING TECHNIQUE USING MWIR EMITTER AND DETECTOR," and U.S. Provisional Application No. 63/093,978, filed Oct. 20, 2020 and entitled, "GAS SENSING SYSTEM HAVING QUADRIC REFLECTIVE SURFACE," both of which are hereby incorporated by reference in their entireties.

TECHNICAL FIELD

The present disclosure relates to detecting a concentration of a gas.

BACKGROUND

There is ongoing effort to improve detecting a concentration of a gas.

Figure 1:
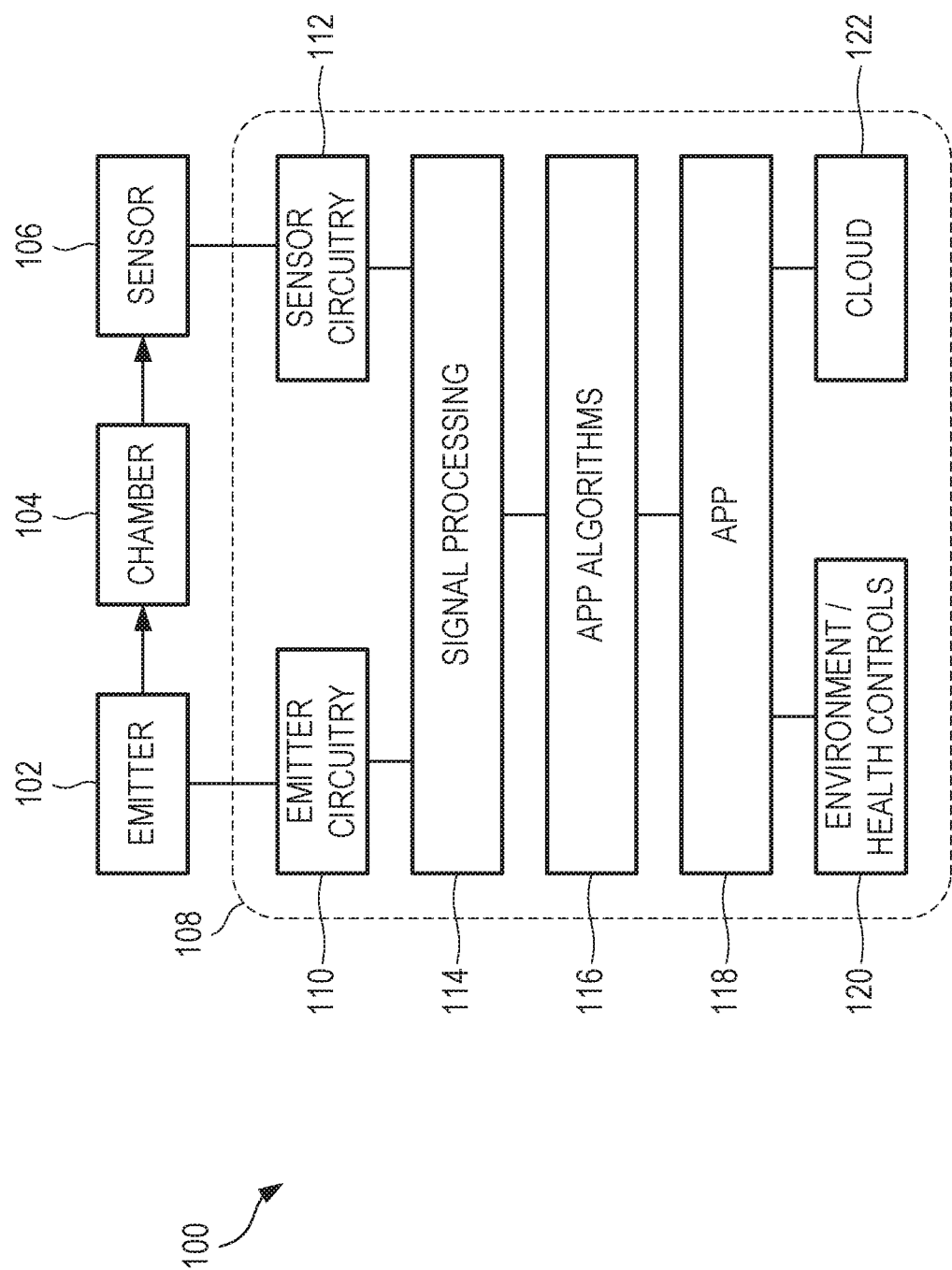
FIG. 1 shows a schematic drawing of an example of a gas sensing system, in accordance with some embodiments.

Corresponding reference characters generally indicate corresponding parts throughout the several views. Elements in the drawings are not necessarily drawn to scale. The configurations shown in the drawings are merely examples and should not be construed as limiting the scope of the disclosed subject matter in any manner.

DETAILED DESCRIPTION

Gas detection is becoming more common for a variety of applications. For example, detecting concentration levels of methane can help guide downstream decisions in the fields of industrial oil and gas exploration, safety, climate change, and others. Detecting concentration levels of formaldehyde and/or volatile organic compounds (VOCs) can help guide downstream decisions in the fields of air quality, safety, and others. Detecting concentration levels of carbon dioxide can help guide downstream decisions in the fields of smart buildings, air quality, capnography, climate change, and others. Detecting concentration levels of carbon monoxide and/or nitrogen dioxide can help guide downstream decisions in the fields of safety and others. Detecting concentration levels of ammonia, sulfur hexafluoride, and/or volatile organic compounds can help guide downstream decisions in the fields of refrigeration, electrical systems, and others. Detecting concentration levels of glucose can help guide downstream decisions in the fields of medicine and others.

Some gas detection systems can make use of a natural absorption of a gas material. For example, methane is found to be absorbent at a wavelength of about 3.3 microns. When a gas sample is illuminated with light at the wavelength of 3.3 microns, methane in the gas sample can absorb some of the illumination. A sensor or detector in the gas detection system can measure the illumination remaining after the illumination passes through the gas sample.

One category of these illumination/detection gas detection systems can be based on the Beer-Lambert Law. In this category, the gas detection system illuminates with light at or near the absorbent wavelength (or with light having a spectrum that includes the absorbent wavelength) and detects how much of the illuminating light passes through the gas sample. Based on the fraction of illuminating light that emerges from the gas sample, the gas detection system can calculate a concentration level of the particular gas in the gas sample.

For gas detection systems based on the Beer-Lambert Law, the sensitivity and/or accuracy can scale with an optical path length over which the absorption can occur. As a result, gas detection systems with larger gas chambers tend to be more sensitive and/or more accurate than those with smaller gas chambers. For example, in a gas detection system in which the gas chamber is hollow, the illumination can progress in a straight line through the gas chamber, such that the optical path length can be comparable to a dimension of the gas chamber.

There is marketplace pressure to shrink the gas detection systems, so that they may be included with more consumer goods, such as in a heating, ventilation, and air conditioning (HVAC) system, a smart speaker, in an automobile (such as in a fuel system, an in-cabin ventilation system, and/or an exhaust system), a refrigeration system, and others.

To decrease the size of the system, various embodiments of the gas detection systems described herein can include a gas chamber through which an optical path can include one or more reflections. For a given length of optical path, the system utilizing an optical path with one or more reflections can be made smaller than a comparable path that lacks such reflections.

In addition, to improve an accuracy of the system, a gas chamber (or one or more reflective surfaces located on or in the gas chamber) can be shaped such that several or all of the optical paths from a light source to a detector traverse a same (or nearly the same) optical path length. For example, a gas chamber can be shaped as an ellipsoid, with a light source located at one of the two foci of the ellipsoid and a detector located the other of the two foci of the ellipsoid. Because the gas chamber (or one or more reflective surfaces located on or in the gas chamber) can be shaped as an ellipsoid, the optical paths that include a single reflection from the gas chamber wall (or the reflective surface or surfaces) can have a same or similar optical path length. More specifically, the optical path lengths can be equal or substantially equal for any optical paths extending from the source, to a location on the surface of the ellipsoid (or the reflective surface or surfaces), to the detector.

In a gas sensing system, a light emitter can emit light through a gas sample toward a concave reflective surface. The reflective surface can redirect the emitted light to propagate through the gas sample toward a light sensor. Using, for example, the Beer-Lambert Law, the system can determine a concentration of the gas material in the gas sample. By selecting a specified shape for the reflective surface, such as a complete or partial ellipsoid, and locating the light emitter and the light sensor in specified locations, such as at one or both foci of the ellipsoid, the gas sensing system can reduce variation in optical path length, from optical path to optical path, in the light that propagates from the light emitter, to the reflective surface, and to the light sensor. Reducing the variation in optical path length can improve an accuracy in determining the concentration of the gas material.

FIG. 1 shows a schematic drawing of an example of a gas sensing system 100, in accordance with some embodiments.

As shown in the example of FIG. 1, an emitter 102 can emit light into a gas chamber 104. The gas chamber 104 can be hollow, and can include optional plumbing (not shown but understandable to a person of ordinary skill in the art) that can direct a gas sample into the gas chamber 104 for measurement, and can extract the gas sample from the gas chamber 104 after measurement. A sensor 106 can detect light, emitted from the emitter 102, that has traversed through the gas sample in the gas chamber 104. At least one processor 108, coupled to the sensor 106, can determine a concentration of a specified gas material in the gas sample.

The emitter 102 can be selected to emit light that can include a wavelength that is relatively strongly absorbed by the gas material that is to be detected.

For example, methane has an absorption peak (e.g., a wavelength at which absorption is relatively large, compared to the absorption at adjacent wavelengths) at a wavelength of about 3.3 microns. To detect a concentration of methane in the gas sample, the emitter 102 can emit light at about 3.3 microns. Similarly, the emitter 102 can emit light at about 3.6 microns to detect formaldehyde and/or volatile organic compounds. The emitter 102 can emit light at about 4.3 microns to detect carbon dioxide. The emitter 102 can emit light at about 4.5 microns to detect carbon monoxide. The emitter 102 can emit light at about 4.7 microns to detect nitrogen dioxide. The emitter 102 can emit light at about 9 microns to detect ammonia, sulfur hexafluoride, and/or certain volatile organic compounds. The emitter 102 can emit light at about 10.4 microns to detect glucose. These numerical examples are but examples. Other suitable wavelengths can also be used to detect other gas materials or compounds.

The emitter 102 can emit light having a spectrum that is relatively sharply peaked. The emitter 102 can emit light having a spectrum that is relatively broad. The emitter 102 can emit light having a spectrum that includes the wavelength at which absorption of the gas material or compound is relatively high. The emitter 102 can emit light in the infrared portion, the visible portion, and/or the ultraviolet portion of the electromagnetic spectrum. The emitter 102 can emit light in the Medium Wavelength Infrared (MWIR) portion of the electromagnetic spectrum, with a wavelength range extending from about 3 microns to about 5 microns. The emitter 102 can emit light in the Long Wavelength Infrared (LWIR) portion of the electromagnetic spectrum, with a wavelength range extending from about 8 microns to about 14 microns.

In various embodiments, the emitter 102 can include one or more light-emitting diodes (LEDs). The one or more light-emitting diodes can include III-V semiconductor materials (or other semiconductor materials from, for example, group II-VI). The one or more light-emitting diodes can include GaSb, InP, InAs, or other suitable materials. The emitter 102 can include one or more lasers. The emitter 102 can include one or more broadband sources that are spectrally filtered.

The sensor 106 can detect light, emitted from the emitter 102, that has traversed through the gas sample in the gas chamber 104. The sensor 106 can include one or more pixels (e.g., detector elements or sensor elements) or other types of sensors known in the art. In some embodiments, the sensor 106 can be separate from the emitter 102. The sensor 106 can include one or more sensor elements that are formed from a same or similar semiconductor material that is used in the emitter 102.

The sensor 106 can optionally be formed integrally with the emitter 102. For example, the sensor 106 and the emitter 102 can both be formed as light-emitting diodes in a single array or in a single integral package. The emitter 102 can be forward biased. The sensor 106 can be reverse biased. Other configurations can also be used.

The at least one processor 108, coupled to the sensor 106, can determine a concentration of a specified gas material in the gas sample.

The at least one processor 108 can include emitter circuitry 110 that can drive the emitter 102.

The at least one processor 108 can include sensor circuitry 112 that can determine a power level of light that strikes the sensor 106. The sensor circuitry 112 can optionally include an analog-to-digital converter.

The at least one processor 108 can include signal processing circuitry 114 that can analyze an output of the sensor circuitry 112. For example, the signal processing circuitry 114 can receive a value that represents a sensed optical power value, and can calculate, from the received value, a concentration level of the gas material in the gas sample. The signal processing circuitry 114 can employ the Beer-Lambert Law to perform the calculation, although other suitable calculations can be performed.

The at least one processor 108 can include one or more application algorithms 116 that can serve as an interface between the signal processing circuitry 114 and an application that includes a user interface.

The at least one processor 108 can include one or more applications 118 that can interface with the one or more application algorithms 116. The one or more application algorithms 116 can communicate with one or more servers dedicated to the environment and/or health controls 120. The one or more application algorithms 116 can communicate with one or more servers connected to the cloud 122.

The gas sensing system 100 can optionally detect two or more gas materials in a same gas sample. The two or more gas materials can have different wavelengths at which the respective gas materials are relatively absorbent. The emitter 102 can emit light at respective two or more wavelengths. The sensor 106 can sense light at the two or more wavelengths. To sense at the wavelengths, the gas sensing system 100 can include one or more wavelength-sensitive filters, such as to direct one wavelength onto one sensor element and direct another wavelength onto another sensor element.

In some examples, the emitter 102 can optionally emit reference light having a spectrum that includes a reference wavelength different from the detection wavelength. The gas sample can interact with the light at the detection wavelength, but may not interact with the reference light at the reference wavelength. The sensor 106 can optionally detect at least some of the reference light. The at least one processor 108 can use the level of the reference light at the sensor 106, in addition to the level of the detection light at the sensor 106, to determine the concentration of the gas material in the gas sample. In some examples, for which the gas sensing system 100 can sense two different gas materials, the emitter can emit a first wavelength and a second wavelength. The wavelengths can be selected such that a first gas interacts with the first wavelength but not the second wavelength and a second gas interacts with the second wavelength but not the first wavelength. Light at the second wavelength can serve as a reference for detecting the first gas, while light at the first wavelength can serve as a reference for detecting the second gas. Other combinations can also be used.

To help ensure that the optical paths lengths from the emitter, to a reflective surface, to the sensor are the same, or approximately the same, for the various optical paths that light can traverse from the emitter to the sensor, the reflective surface can be shaped to include a portion of a quadric surface (e.g., a surface having a cross-section that is a conic section). Suitable quadric surfaces include ellipsoids and paraboloids, as described in detail below. The reflective surfaces discussed herein can be substantially smooth, such that a majority of light that reflects from the reflective surface does so with specular (e.g., non-diffuse or non-scattering) reflection (e.g., where a single incident ray can produce a single exiting ray in a single direction), rather than diffuse reflection (e.g., where a single incident ray can produce multiple exiting rays in a range of directions).

Figure 2:
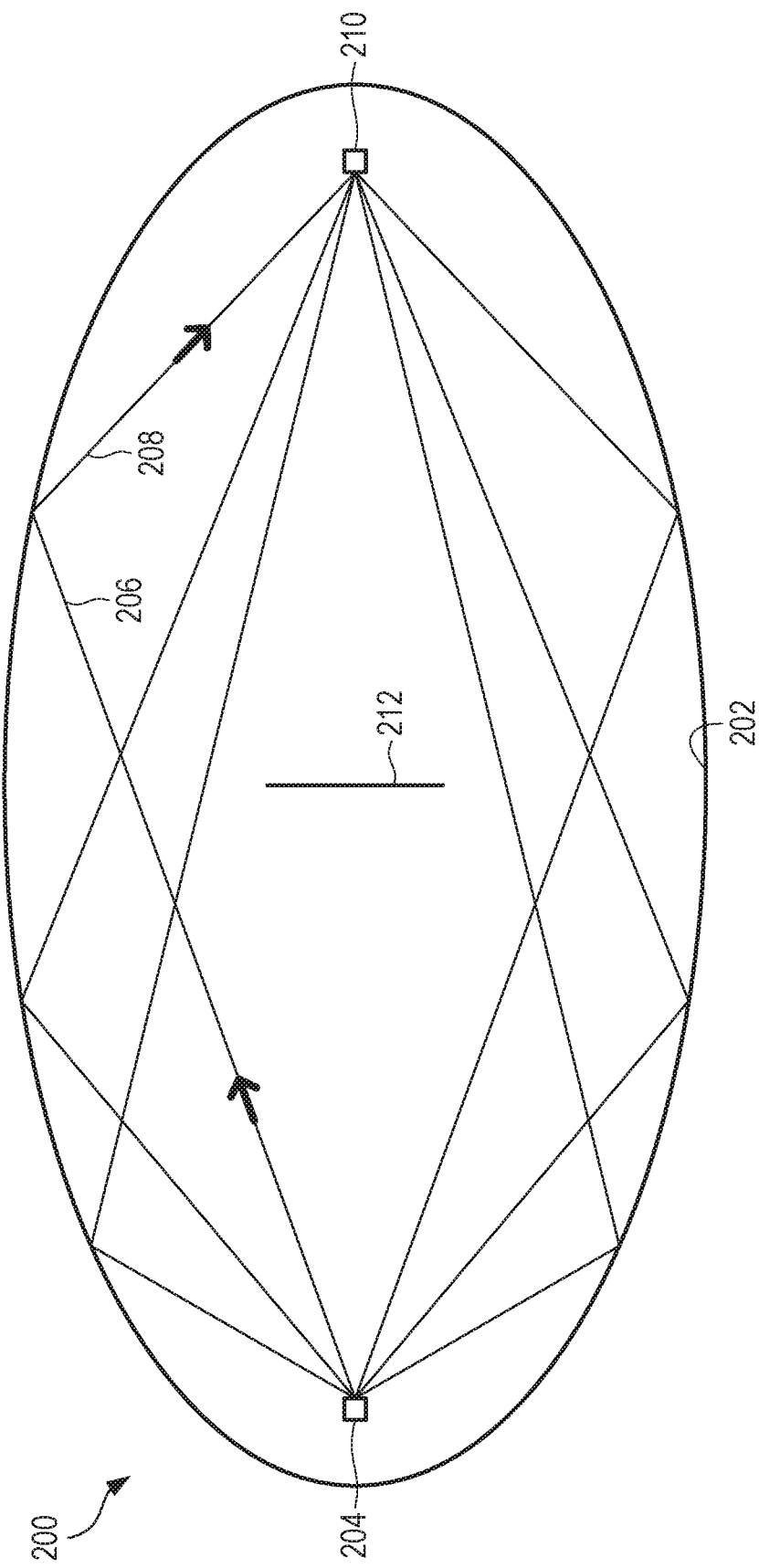
FIG. 2 shows a cross-sectional side view of an example of a gas sensing system, in accordance with some embodiments.

FIG. 2 shows a cross-sectional side view of an example of a gas sensing system 200, in accordance with some embodiments. FIG. 2, as well as FIGS. 3-8 below, omits the circuitry of the gas sensing system 200; any suitable circuitry can also be used as will be recognized by a person of ordinary skill in the art upon reading and understanding the disclosed subject matter. Similarly, FIG. 2, as well as FIGS. 3-8 below, omits plumbing of the gas chamber, which can controllably pump a gas sample into the gas chamber and can controllably pump the gas sample out of the gas chamber, after a measurement has been taken.

In the configuration of FIG. 2, the gas sensing system 200 can include a reflective surface 202 that is shaped to include all or part of an ellipsoid. Specifically, the ellipsoid has an elongation axis, such that a cross-section taken orthogonal to the elongation axis is generally circular, and a cross-section taken in a plane that includes the elongation axis is elliptical. The ellipsoid includes two foci that are spaced apart along the elongation axis. The reflective surface is shaped such that every light ray, or nearly every light ray, that originates at one focus specularly reflects off the ellipsoidal reflective surface to be directed to the other focus. Further, the reflective surface is shaped such that each optical path between the two foci, including one reflection from the ellipsoidal reflective surface, has a same or nearly a same value of optical path length.

In some examples, the reflective surface 202 is a wall of the gas chamber. In other examples, the reflective surface 202 can be contained inside the gas chamber, such as by being a structure that can reflect light without constraining the gas sample or defining a volume of the gas chamber. In other examples, the reflective surface 202 can be outside the gas chamber, such as by forming the wall of the gas chamber by a material that is transparent or substantially transparent at the emitted wavelength or wavelengths, such as plastic or glass, which constrains the gas sample but allows light to exit and re-enter the gas chamber.

In some examples in which the reflective surface 202 is a complete or partial ellipsoid, a light emitter 204 can be located at or near a first focus of the ellipsoid. The light emitter 204 can be the same or similar to the emitter 102 of FIG. 1. Although as shown, the light emitter 204 emits light generally in a direction toward the light sensor 210, in other embodiments the light may be emitted in substantially all directions simultaneously. The light emitter 204 can emit first light 206 into the gas sample. The first light 206 can propagate away from the light emitter 204, through the gas sample, in a range of propagation directions. The first light 206 can specularly reflect (e.g., reflect without scattering, such that light with a single incident direction can reflect with a single exiting direction) from the reflective surface 202 to form second light 208. Because the reflective surface 202 can be a complete or partial ellipsoid, the second light 208 can be directed toward a second focus of the ellipsoid, for most or all of the propagation directions of the first light 206. The second light 208 can propagate, through the gas sample, toward the second focus of the ellipsoid.

In the configuration of FIG. 2, a light sensor 210 can be located at or near the second focus of the ellipsoid, to collect most or all of the second light 208. The light sensor 210 may the same as or similar to the light sensor 106 of FIG. 1. The collected light will have traversed one of a range of optical paths from the first focus, to the reflective surface 202, to the second focus. Because the reflective surface 202 can be a complete or partial ellipsoid, the range of optical paths can have a path length that is the same or nearly the same, for most or all of the optical paths, regardless of propagation direction away from the light emitter 204.

In order to prevent light from propagating directly from the light emitter 204 to the light sensor 210, an optional light baffle 212 can block such light, such that the only light arriving at the light sensor 210 is light that has reflected one time from the reflective surface 202.

In the configuration of FIG. 2, the light emitter 204 is oriented to emit light generally toward the light sensor 210 (e.g., with an angular emission pattern that peaks along an elongation axis of the ellipsoid and decreases at angles away from the elongation axis). It is possible to use different orientations for the light emitter 204, which can illuminate different portions of the reflective surface 202, and in turn illuminate different portions of the volume of the gas chamber.

In some examples, it is possible to eliminate portions of the reflective surface 202 that would receive little or no illumination, which can reduce the size of the gas sensing system 200.

Figure 3:
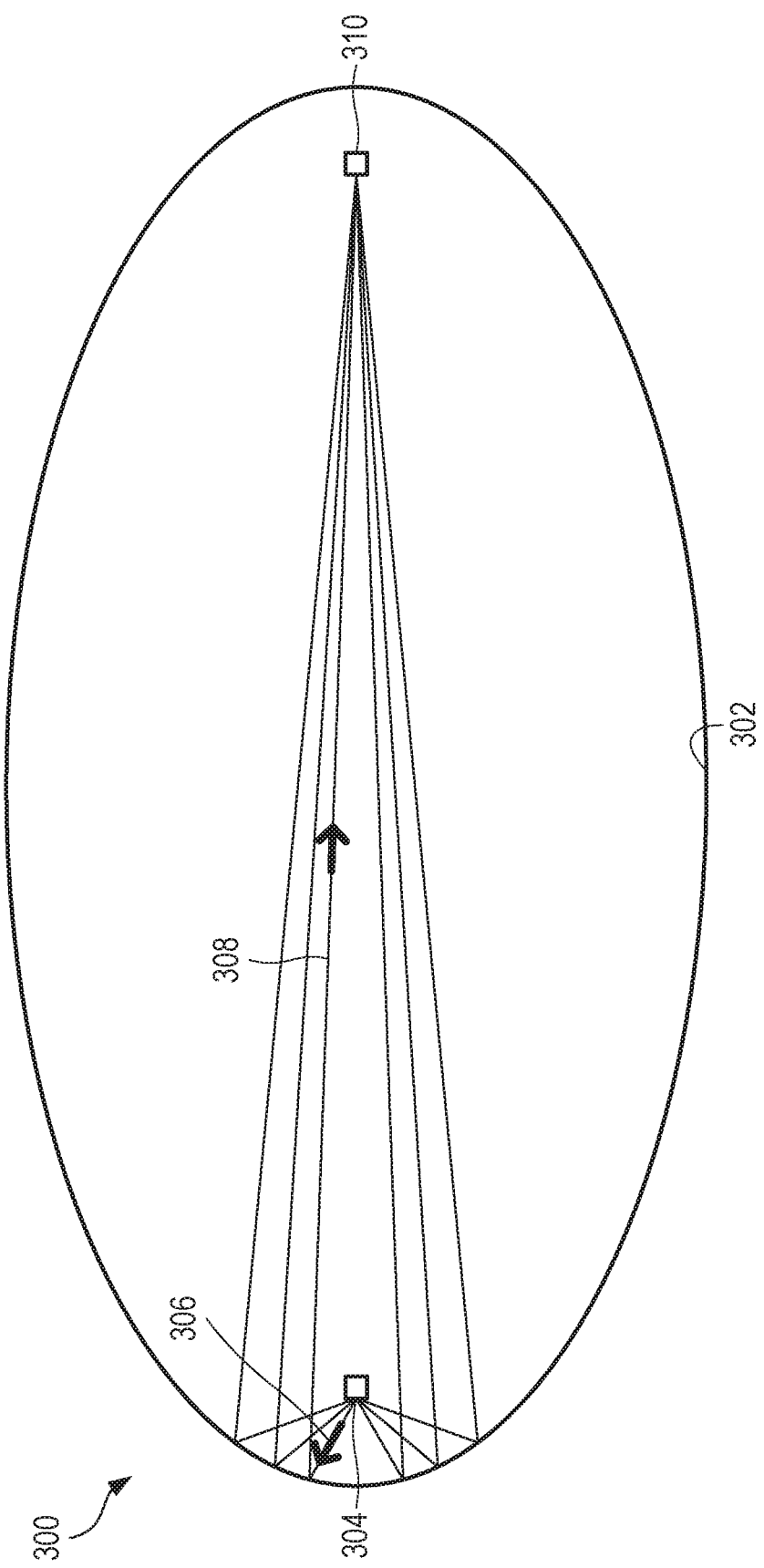
FIG. 3 shows a cross-sectional side view of an example of a gas sensing system, in accordance with some embodiments.

FIG. 3 shows a cross-sectional side view of an example of a gas sensing system 300, in accordance with some embodiments. Compared with the configuration of FIG. 2, the system 300 includes a light emitter 304 that emits light away from the light sensor 310, rather than toward the light sensor. As a result, essentially all of the emitted light is reflected by the reflective surface 302, and the optional light baffle 212 of FIG. 2 can be omitted.

The reflective surface 302 can be a complete or partial ellipsoid. A light emitter 304 can be located at or near a first focus of the ellipsoid. The light emitter 304 can emit first light 306 into the gas sample. The light emitter 304 can be the same as or similar to the emitter 102 of FIG. 1 and/or the emitter 204 of FIG. 2. (Similarly, the light emitters shown in the remainder of the figures can also be the same as or similar to the emitter 102 of FIG. 1 and/or the emitter 204 of FIG. 2.) The first light 306 can propagate away from the light emitter 304, through the gas sample, in a range of propagation directions. The first light 306 can specularly reflect from the reflective surface 302 to form second light 308. Because the reflective surface 302 can be a complete or partial ellipsoid, the second light 308 can be directed toward a second focus of the ellipsoid, for most or all of the propagation directions of the first light 306. The second light 308 can propagate, through the gas sample, toward the second focus of the ellipsoid. A light sensor 310 can be located at or near the second focus of the ellipsoid, to collect most or all of the second light 308. The light sensor 310 may the same as or similar to the light sensor 106 of FIG. 1 and/or the light sensor 210 of FIG. 2. (Similarly, the light sensors shown in the remainder of the figures can also be the same as or similar to the light sensor 106 of FIG. 1 and/or the light sensor 210 of FIG. 2.) The collected light will have traversed one of a range of optical paths from the first focus, to the reflective surface 302, to the second focus. Because the reflective surface 302 can be a complete or partial ellipsoid, the range of optical paths can have a path length that is the same or nearly the same, for most or all of the optical paths, regardless of propagation direction away from the light emitter 304.

Figure 4:
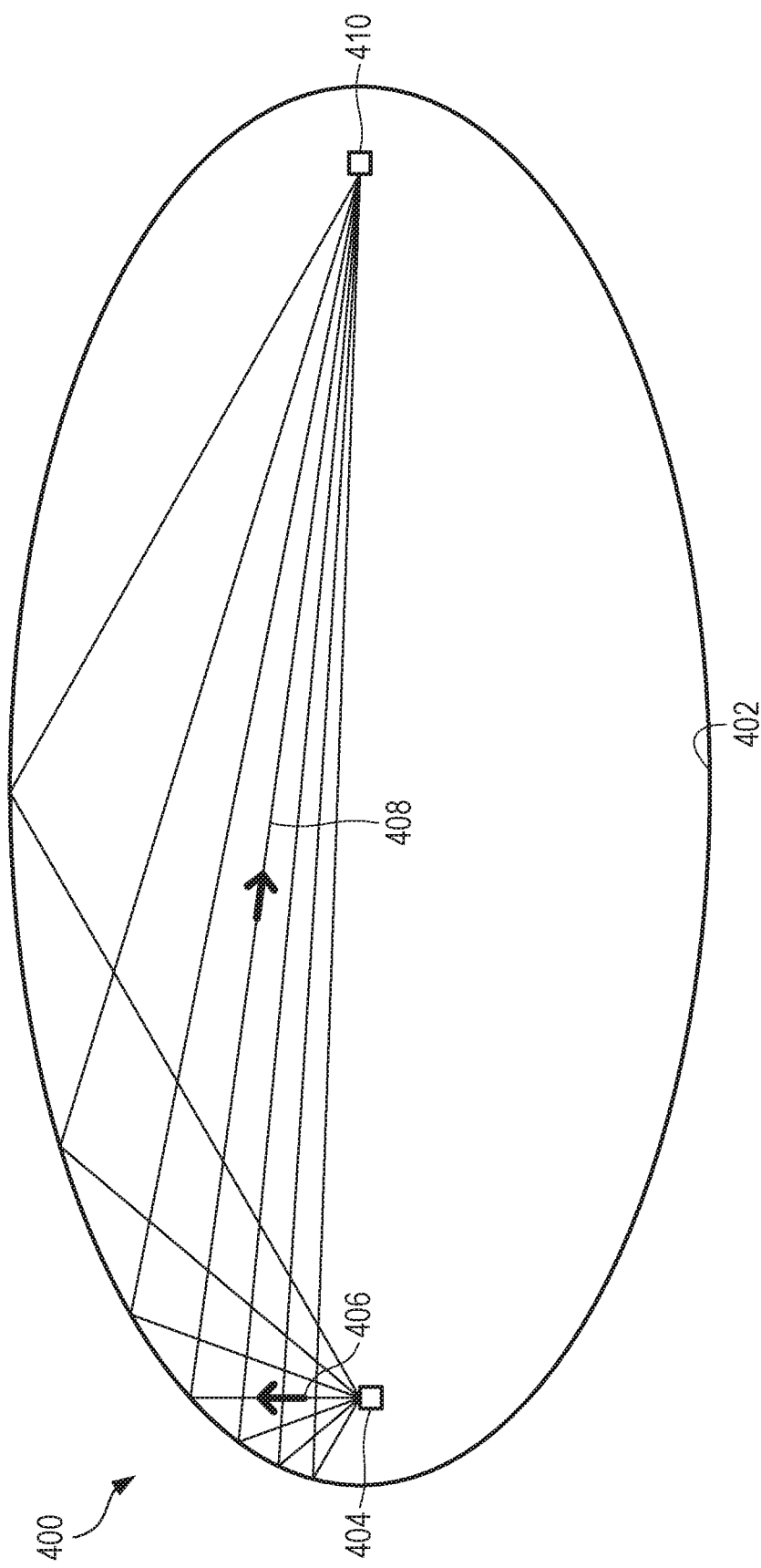
FIG. 4 shows a cross-sectional side view of an example of a gas sensing system, in accordance with some embodiments.

FIG. 4 shows a cross-sectional side view of an example of a gas sensing system 400, in accordance with some embodiments. Compared with the configuration of FIGS. 2 and 3, the system 400 includes a light emitter 404 that emits light generally orthogonal to the elongation axis of the ellipsoid (e.g., with an angular emission pattern that peaks along a direction that is generally orthogonal to the elongation axis of the ellipsoid and decreases at angles away from the peak direction). As a result, essentially all of the emitted light is reflected by the reflective surface 402, and the optional light baffle 212 of FIG. 2 can be omitted.

The reflective surface 402 can be a complete or partial ellipsoid. A light emitter 404 can be located at or near a first focus of the ellipsoid. The light emitter 404 can emit first light 406 into the gas sample. The first light 406 can propagate away from the light emitter 404, through the gas sample, in a range of propagation directions. The first light 406 can specularly reflect from the reflective surface 402 to form second light 408. Because the reflective surface 402 can be a complete or partial ellipsoid, the second light 408 can be directed toward a second focus of the ellipsoid, for most or all of the propagation directions of the first light 406. The second light 408 can propagate, through the gas sample, toward the second focus of the ellipsoid. A light sensor 410 can be located at or near the second focus of the ellipsoid, to collect most or all of the second light 408. The collected light will have traversed one of a range of optical paths from the first focus, to the reflective surface 402, to the second focus. Because the reflective surface 402 can be a complete or partial ellipsoid, the range of optical paths can have a path length that is the same or nearly the same, for most or all of the optical paths, regardless of propagation direction away from the light emitter 404.

Because it is possible to eliminate portions of the reflective surface 402 that would receive little or no illumination, the configuration of FIG. 4 can optionally eliminate about half of the reflective surface 402. Doing so can allow the gas chamber of the system 400 to shrink in size to about half of the full ellipsoid.

In the configurations of FIGS. 2-4, the light emitter and the light sensor are located at or near different foci of the ellipsoid. Alternatively, it is possible to position both the light emitter and the light sensor at or near just one of the foci. In these examples, the collected light will have traversed one of a range of optical paths from the first focus, to the reflective surface, to and through the second focus, to the reflective surface, to return to the first focus. Because the reflective surface can be a complete or partial ellipsoid, the range of optical paths can have a path length that is the same or nearly the same, for most or all of the optical paths, regardless of propagation direction away from the light emitter. The configuration with the light emitter and the light sensor both located at the same focus can have an optical path length that is about twice as large for the configuration in with the light emitter and the light sensor being at different foci.

Figure 5:
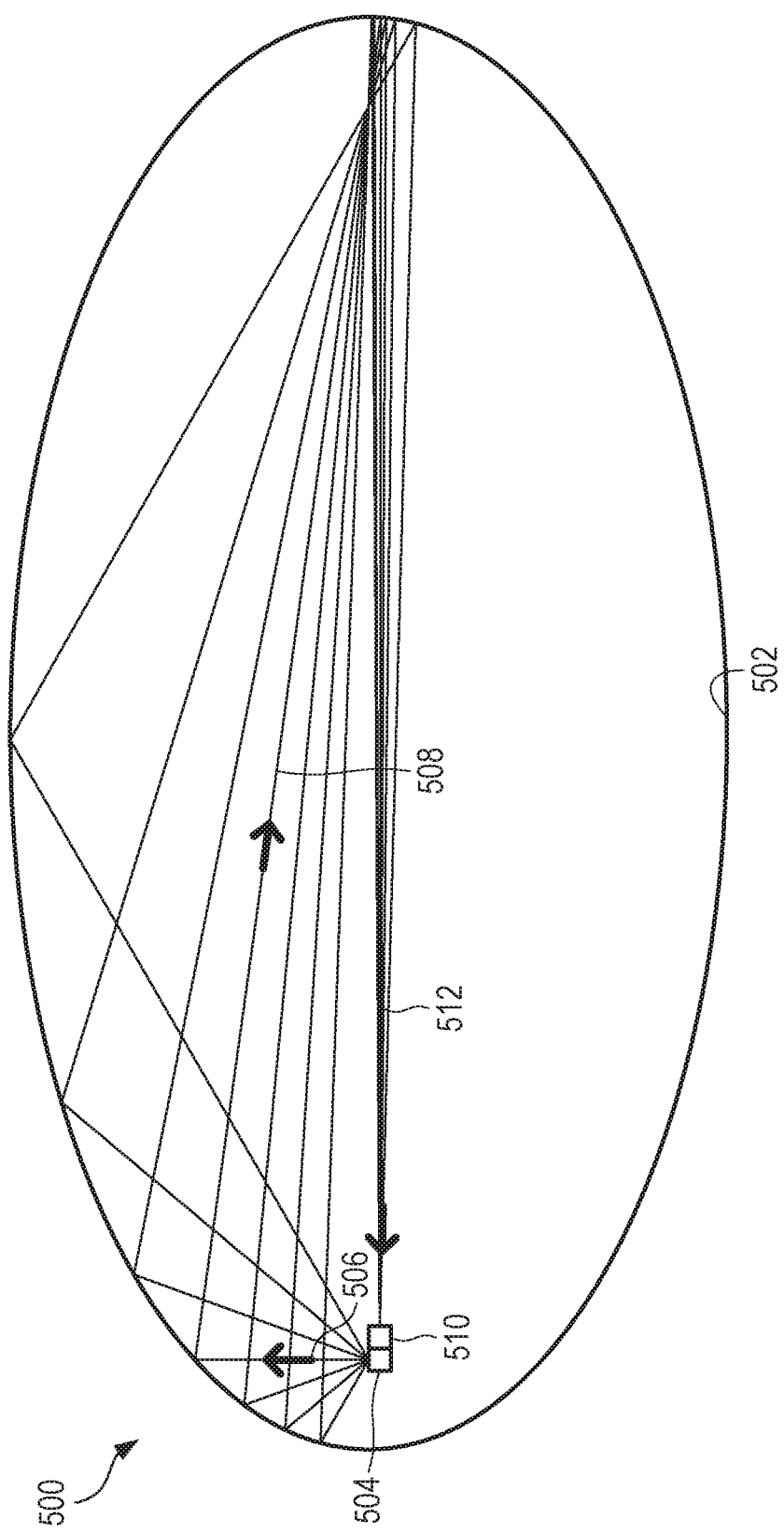
FIG. 5 shows a cross-sectional side view of an example of a gas sensing system, in accordance with some embodiments.

FIG. 5 shows a cross-sectional side view of an example of a gas sensing system 500, in accordance with some embodiments. Compared with the configuration of FIGS. 2-4, the system 500 includes a light emitter 504 and a light sensor 510 that are both positioned at a single focus of the ellipsoid defined by the reflective surface 502.

The reflective surface 502 can be a complete or partial ellipsoid. A light emitter 504 can be located at or near a first focus of the ellipsoid. The light emitter 504 can emit first light 506 into the gas sample. The first light 506 can propagate away from the light emitter 504, through the gas sample, in a range of propagation directions. The first light 506 can specularly reflect from the reflective surface 502 to form second light 508. Because the reflective surface 502 can be a complete or partial ellipsoid, the second light 508 can be directed toward a second focus of the ellipsoid, for most or all of the propagation directions of the first light 506. The second light 508 can propagate, through the gas sample, toward the second focus of the ellipsoid. The second light 508 can then propagate through the second focus, to reflect a second time from the reflective surface 502 to form third light 512. A light sensor 510 can be located at or near the first focus of the ellipsoid, to collect most or all of the third light 512. The collected light will have traversed one of a range of optical paths from the first focus, to the reflective surface 502, to and through the second focus, to the reflective surface 502, and back to the first focus. Because the reflective surface 502 can be a complete or partial ellipsoid, the range of optical paths can have a path length that is the same or nearly the same, for most or all of the optical paths, regardless of propagation direction away from the light emitter 504.

In the configuration of FIG. 5, the light sensor 510 can be located centered on the elongation axis of the ellipsoid and adjacent to the light emitter 504, laterally offset from the elongation axis, or in any suitable location that is adjacent or approximately adjacent to the light emitter 504. In some examples, the light emitter 504 and the light sensor 510 can optionally be formed on a same substrate.

The configurations of FIGS. 2-5 have utilized a reflective surface that is ellipsoidal or substantially ellipsoidal. As an alternative, the gas sensing system can include a reflective surface that is shaped to include a complete or partial paraboloid. Specifically, the paraboloid has a central axis, such that a cross-section taken orthogonal to the central axis is generally circular, and a cross-section taken in a plane that includes the central axis is a parabola. The paraboloid includes one focus that is located along the central axis. The reflective surface is shaped such that every light ray or nearly every light ray that originates at the focus specularly reflects off the paraboloid reflective surface to be directed to be parallel or substantially parallel to the central axis. Further, the reflective surface is shaped such that each optical path from the focus, including one reflection from the ellipsoidal reflective surface, to a plane that is orthogonal to the central axis, has a same or nearly a same value of optical path length.

Figure 6:
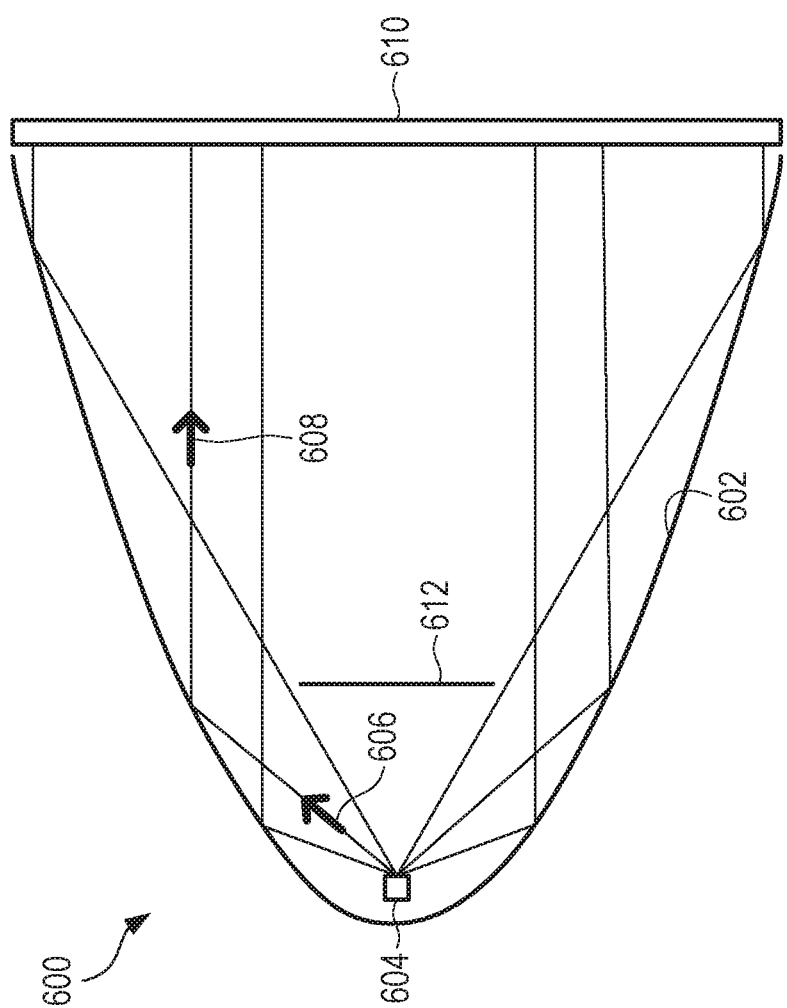
FIG. 6 shows a cross-sectional side view of an example of a gas sensing system, in accordance with some embodiments.

FIG. 6 shows a cross-sectional side view of an example of a gas sensing system 600, in accordance with some embodiments. Compared with the configuration of FIGS. 2-5, the system 600 includes a reflective surface that is paraboloidal, rather than ellipsoidal.

The reflective surface 602 can be a partial paraboloid. (Note that full paraboloids are infinite in extent.) A light emitter 604 can be located at or near a focus of the paraboloid. The light emitter 604 can emit first light 606 into the gas sample. The first light 606 can propagate away from the light emitter 604, through the gas sample, in a range of propagation directions. The first light 606 can specularly reflect from the reflective surface 602 to form second light 608. Because the reflective surface 602 can be a partial paraboloid, the second light 608 can be directed to propagate generally parallel to a central axis of the paraboloid, for most or all of the propagation directions of the first light 606. The second light 608 can propagate, through the gas sample, generally away from the light emitter 604. A light sensor 610 can receive the second light 608. In the configuration of FIG. 6, the light sensor 610 can be relatively large (compared to the light emitter 604), so as to collect all of the second light 608. The collected light will have traversed one of a range of optical paths from the focus, to the reflective surface 602, to the light sensor 610. Because the reflective surface 602 can be a partial paraboloid, the range of optical paths can have a path length that is the same or nearly the same, for most or all of the optical paths, regardless of propagation direction away from the light emitter 604.

In order to prevent light from propagating directly from the light emitter 604 to the light sensor 610, an optional light baffle 612 can be sized and located to block such light, such that the only light arriving at the light sensor 610 is light that has reflected one time from the reflective surface 602. The light baffle 612 can be the same or similar to the light baffle 212 of FIG. 2.

In the configuration of FIG. 6, the light emitter 604 is oriented to emit light generally toward the light sensor 610 (e.g., with an angular emission pattern that peaks along a central axis of the paraboloid and decreases at angles away from the central axis). However, a person of ordinary skill in the art will recognize that a light emitter that emits 360 degrees, or some subset thereof, may be used as well. A complete solid angle of $4\pi$ steradians can also be considered. It is possible to use different orientations for the light emitter 604, which can illuminate different portions of the reflective surface 602, and in turn illuminate different portions of the volume of the gas chamber.

Figure 7:
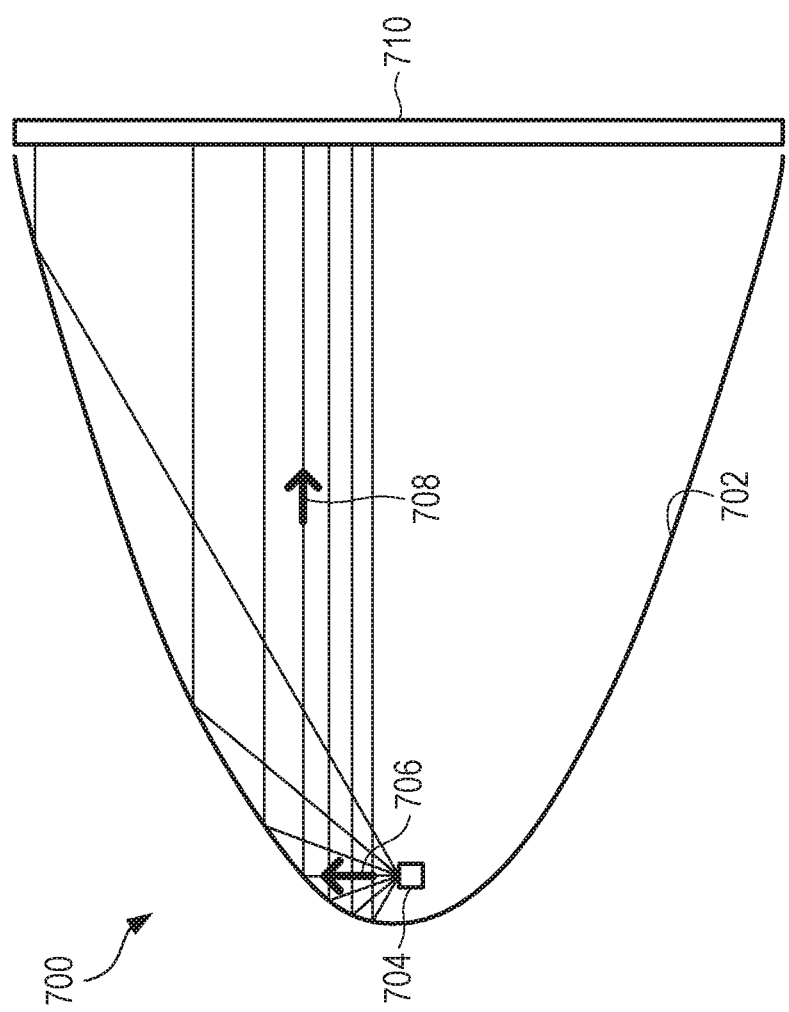
FIG. 7 shows a cross-sectional side view of an example of a gas sensing system, in accordance with some embodiments.

FIG. 7 shows a cross-sectional side view of an example of a gas sensing system 700, in accordance with some embodiments. Compared with the configuration of FIG. 6, the system 700 includes a light emitter 704 that emits generally orthogonal to the central axis of the paraboloid (e.g., with an angular emission pattern that peaks along a direction that is generally orthogonal to the central axis of the paraboloid and decreases at angles away from the peak direction). As a result, essentially all of the emitted light is reflected by the reflective surface 702, and the optional light baffle 612 of FIG. 6 can be omitted.

The reflective surface 702 can be a partial paraboloid. A light emitter 704 can be located at or near a focus of the paraboloid. The light emitter 704 can emit first light 706 into the gas sample. The first light 706 can propagate away from the light emitter 704, through the gas sample, in a range of propagation directions. The first light 706 can specularly reflect from the reflective surface 702 to form second light 708. Because the reflective surface 702 can be a partial paraboloid, the second light 708 can be directed to propagate generally parallel to a central axis of the paraboloid, for most or all of the propagation directions of the first light 706. The second light 708 can propagate, through the gas sample, generally away from the light emitter 704. A light sensor 710 can receive the second light 708. In the configuration of FIG. 7, the light sensor 710 can be relatively large (compared to the light emitter 704), so as to collect all of the second light 708. The collected light will have traversed one of a range of optical paths from the focus, to the reflective surface 702, to the light sensor 710. Because the reflective surface 702 can be a partial paraboloid, the range of optical paths can have a path length that is the same or nearly the same, for most or all of the optical paths, regardless of propagation direction away from the light emitter 704.

In the configurations of FIGS. 6 and 7, the locations of the light emitter and the light sensor can optionally be swapped, such that the light sensor is located proximate the focus of the paraboloid, and the light emitter has an emitting area that is arranged generally orthogonal to the central axis.

In the configurations of FIGS. 6 and 7, the light sensor can be a relatively large light sensor, with a surface area that is large enough to capture most or all of the second light. As an alternative, an optional lens can focus the second light onto a relatively small light sensor. In some examples, the relatively small light sensor may have lower noise and/or a faster response time than the relatively large light sensor.

Figure 8:
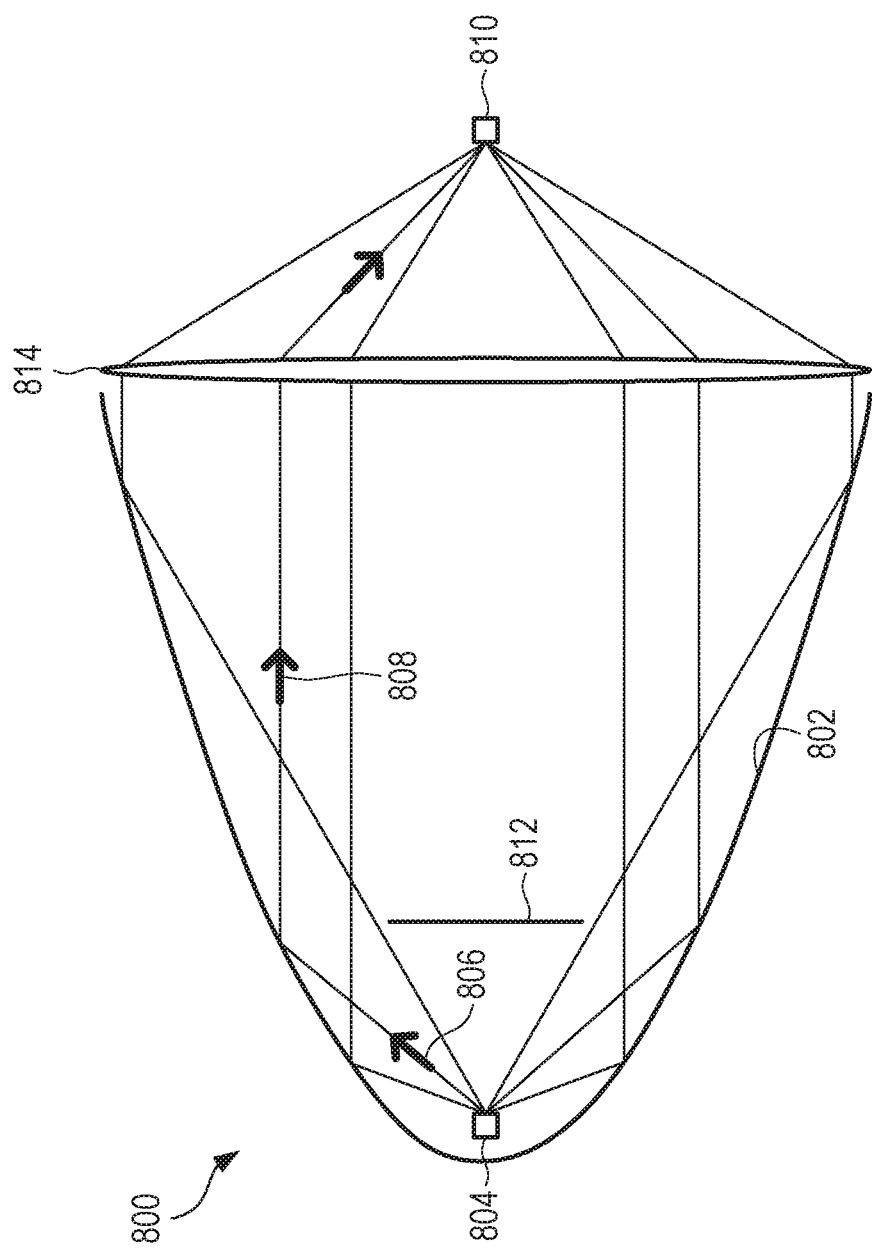
FIG. 8 shows a cross-sectional side view of an example of a gas sensing system, in accordance with some embodiments.

FIG. 8 shows a cross-sectional side view of an example of a gas sensing system 800, in accordance with some embodiments. Compared with the configuration of FIG. 7, the system 800 includes a lens 814 that can focus the second light 808 onto a smaller light sensor 810 than the relatively large light sensor 710 of FIG. 7.

The reflective surface 802 can be a partial paraboloid. A light emitter 804 can be located at or near a focus of the paraboloid. The light emitter 804 can emit first light 806 into the gas sample. The first light 806 can propagate away from the light emitter 804, through the gas sample, in a range of propagation directions. The first light 806 can specularly reflect from the reflective surface 802 to form second light 808. Because the reflective surface 802 can be a partial paraboloid, the second light 808 can be directed to propagate generally parallel to a central axis of the paraboloid, for most or all of the propagation directions of the first light 806. The second light 808 can propagate, through the gas sample, generally away from the light emitter 804. The lens 814, such as a refractive lens or a Fresnel lens, or a combination of lenses, can focus the second light onto a relatively small light sensor 810. The light arriving at the light sensor 810 will have traversed one of a range of optical paths from the focus, to the reflective surface 802, through the lens 814, to the light sensor 810. Because the reflective surface 802 can be a partial paraboloid, the range of optical paths can have a path length that is the same or nearly the same, for most or all of the optical paths, regardless of propagation direction away from the light emitter 804.

In order to prevent light from propagating directly from the light emitter 804 to the light sensor 810, an optional light baffle 812 can block such light, such that the only light arriving at the light sensor 810 is light that has reflected one time from the reflective surface 802. The light baffle 812 can be the same or similar to the light baffle 212 of FIG. 2 and/or the light baffle 612 of FIG. 6.

In some examples, the lens 814 and the light sensor 810 can be located outside the gas chamber. For example, the gas chamber can include a transparent wall, which can contain the gas sample but allow the second light 808 to pass through the transparent wall. The lens 814 can be formed integrally with the transparent wall, or can be formed separately from the transparent wall.

The configurations of FIGS. 2-8 can include a reflective surface that is generally smooth, so as to provide specular (e.g., non-diffusive) reflection. The reflective surface can be shaped as at least a portion of a quadric surface (e.g., a surface having a cross-section that is a conic section), such as an ellipsoid or a paraboloid. Shaping the reflective surface in this manner can reduce or eliminate path-to-path variations in the lengths of the various optical paths that extend from the light emitter, through the gas sample and reflecting from the reflective surface, to the light sensor. By reducing or eliminating these optical path length variations, the system can more accurately use the Beer-Lambert Law to determine the concentration of the gas material in the gas sample.

In any of the configurations shown in FIGS. 2-8, the locations of the light emitter and the light sensor can be swapped. For example, the configurations of FIGS. 6 and 7 can utilize a relatively large light emitter in place of the relatively large light sensor, and can use a relatively small light sensor located at the focus of the paraboloid. Other configurations can also be used.

Figure 9:
FIG. 9 shows a flow chart of an example of a method for measuring a concentration of a gas material in a gas sample, in accordance with some embodiments.

FIG. 9 shows a flow chart of an example of a method 900 for measuring a concentration of a gas material in a gas sample, in accordance with some embodiments. The gas material can have an absorption peak at a first wavelength. The method can be executed on any of the gas sensing systems discussed herein, or on other suitable gas sensing systems.

At operation 902, the method 900 can include emitting first light having a spectrum that includes the first wavelength.

At operation 904, the method 900 can include specularly reflecting, from a reflective surface of a gas chamber, at least some of the first light to form second light, the reflective surface being concave and having a shape that is at least a portion of a quadric surface.

At operation 906, the method 900 can include detecting at least some of the second light.

While exemplary embodiments of the present disclosed subject matter have been shown and described herein, it will be obvious to those skilled in the art that such embodiments are provided by way of example only. Numerous variations, changes, and substitutions will now occur to those skilled in the art, upon reading and understanding the material provided herein, without departing from the disclosed subject matter. It should be understood that various alternatives to the embodiments of the disclosed subject matter described herein may be employed in practicing the various embodiments of the subject matter. It is intended that the following claims define the scope of the disclosed subject matter and that methods and structures within the scope of these claims and their equivalents be covered thereby.

What is claimed is:

1. A gas sensing system, comprising: an emitter configured to emit first light; a gas chamber that includes a reflective surface configured to specularly reflect the first light to form second light, the reflective surface being concave and having a shape that is at least a portion of an ellipsoid that includes a first focus and a second focus, the reflective surface being configured to direct the second light toward the second focus of the ellipsoid, pass the second light through the second focus of the ellipsoid, and reflect the second light to form third light;
a sensor configured to detect at least some of the third light, the emitter and the sensor being located proximate the first focus; and
at least one processor configured to determine a concentration of a gas material in a gas sample in the gas chamber from a level of the third light at the sensor.

2. The gas sensing system of claim 1, wherein:
the emitter is further configured to emit reference light having a spectrum that differs from a spectrum of the first light;
the sensor is further configured to detect at least some of the reference light; and
the at least one processor is further configured to use a level of the reference light at the sensor, in addition to the level of the third light at the sensor, to determine the concentration of the gas material in the gas sample.

3. The gas sensing system of claim 1, wherein the at least one processor is further configured to determine the concentration from the Beer-Lambert Law.

4. A method, comprising: emitting first light; specularly reflecting, from a reflective surface of a gas chamber, at least some of the first light to form second light, the reflective surface being concave and having a shape that is at least a portion of an ellipsoid that includes a first focus and a second focus, the first light being emitted by an emitter located proximate the first focus; directing, with the reflective surface, the second light toward the second focus of the ellipsoid; passing the second light through the second focus of the ellipsoid; reflecting the second light from the reflective surface to form third light; directing the third light onto a sensor located proximate the first focus;
detecting at least some of the third light with the sensor; and
determining a concentration of a gas material in a gas sample in the gas chamber, using at least one processor, from a level of the third light at the sensor and from the Beer-Lambert Law.

5. A gas sensing system, comprising:
an emitter configured to emit first light having a spectrum that includes at least a first wavelength;
a gas chamber that includes a reflective surface configured to reflect the first light to form second light, the reflective surface being concave and having a shape that is at least a portion of an ellipsoid that has a first focus and a second focus, the emitter being positioned at the first focus, the reflective surface being configured to direct the second light toward the second focus of the ellipsoid, pass the second light through the second focus of the ellipsoid, and reflect the second light to form third light;
a sensor positioned at the first focus and configured to detect at least some of the third light; and
at least one processor configured to determine a concentration of a gas material in the gas sample from a level of the third light at the sensor and from the Beer-Lambert Law, the gas material having an absorption peak at the first wavelength.

6. The gas sensing system of claim 5, wherein:

the emitter is further configured to emit reference light having a spectrum that includes a second wavelength different from the first wavelength;

the sensor is further configured to detect at least some of the reference light; and the processor is further configured to use a level of the reference light at the sensor, in addition to the level of the third light at the sensor, to determine the concentration of the gas material in the gas sample.

7. The gas sensing system of claim 1, wherein the sensor is centered on an elongation axis of the ellipsoid and adjacent to the emitter.

8. The gas sensing system of claim 1, wherein the sensor is laterally offset from elongation axis of the ellipsoid and adjacent to the emitter.

9. The gas sensing system of claim 1, wherein the emitter and the sensor are formed on a same substrate.

10. The method of claim 4, wherein the sensor is centered on an elongation axis of the ellipsoid and adjacent to the emitter.

11. The method of claim 4, wherein the sensor is laterally offset from elongation axis of the ellipsoid and adjacent to the emitter.

12. The method of claim 4, wherein the emitter and the sensor are formed on a same substrate.

13. The gas sensing system of claim 5, wherein the sensor is centered on an elongation axis of the ellipsoid and adjacent to the emitter.

14. The gas sensing system of claim 5, wherein the sensor is laterally offset from elongation axis of the ellipsoid and adjacent to the emitter.

15. The gas sensing system of claim 5, wherein the emitter and the sensor are formed on a same substrate.

16. The gas sensing system of claim 1, wherein the reflective surface is concave over a full extent of the reflective surface.

* * * * *

UNITED STATES PATENT AND TRADEMARK OFFICE
CERTIFICATE OF CORRECTION

PATENT NO. : 11,740,179 B2
APPLICATION NO. : 17/090118
DATED : August 29, 2023
INVENTOR(S) : Masui et al.

Page 1 of 1

It is certified that error appears in the above-identified patent and that said Letters Patent is hereby corrected as shown below:

In the Claims

In Column 11, Line 65, in Claim 1, after "comprising:", insert a linebreak

In Column 11, Line 66, in Claim 1, after "light;", insert a linebreak

In Column 12, Line 28, in Claim 4, after "comprising:", insert a linebreak

In Column 12, Line 28, in Claim 4, after "light;", insert a linebreak

In Column 12, Line 35, in Claim 4, after "focus;", insert a linebreak

In Column 12, Line 37, in Claim 4, after "ellipsoid;", insert a linebreak

In Column 12, Line 38, in Claim 4, after "ellipsoid;", insert a linebreak

In Column 12, Line 39, in Claim 4, after "light;", insert a linebreak

Signed and Sealed this
Twenty-fourth Day of October, 2023

Katherine Kelly Vidal

Katherine Kelly Vidal
*Director of the United States Patent and Trademark Office*